United States Patent
Li et al.

(10) Patent No.: US 9,630,942 B2
(45) Date of Patent: Apr. 25, 2017

(54) TECHNOLOGICAL METHOD FOR SYNTHESIS OF OPTICALLY PURE L-/D-LACTIDE CATALYZED BY BIOGENIC GUANIDINE

(71) Applicant: Nanjing University, Nanjing, Jiangsu (CN)

(72) Inventors: Hong Li, Jiangsu (CN); Quanxing Zhang, Jiangsu (CN); Na Cheng, Jiangsu (CN); Tianrong Zhang, Jiangsu (CN); Wei Jiang, Jiangsu (CN); Wei Huang, Jiangsu (CN); Bingcai Pan, Jiangsu (CN)

(73) Assignee: Nanjing University, Nanjing, Jiangsu (CN)

( * ) Notice: Subject to any disclaimer, the term of this patent is extended or adjusted under 35 U.S.C. 154(b) by 0 days.

(21) Appl. No.: 14/782,627

(22) PCT Filed: Aug. 17, 2013

(86) PCT No.: PCT/CN2013/081710
§ 371 (c)(1),
(2) Date: Oct. 6, 2015

(87) PCT Pub. No.: WO2014/173047
PCT Pub. Date: Oct. 30, 2014

(65) Prior Publication Data
US 2016/0039782 A1    Feb. 11, 2016

(30) Foreign Application Priority Data

Apr. 24, 2013 (CN) .......................... 2013 1 0146469

(51) Int. Cl.
*C07D 319/12* (2006.01)
*B01J 31/02* (2006.01)

(52) U.S. Cl.
CPC ........ *C07D 319/12* (2013.01); *B01J 31/0208* (2013.01); *B01J 31/0241* (2013.01); *B01J 31/0271* (2013.01); *B01J 2231/34* (2013.01)

(58) Field of Classification Search
CPC . C07D 319/12; B01J 31/0241; B01J 31/0208; B01J 31/0271; B01J 2231/34
See application file for complete search history.

(56) References Cited

U.S. PATENT DOCUMENTS 5,053,522 A    10/1991    Muller

FOREIGN PATENT DOCUMENTS

| CN | 101903370 | 12/2010 |
| CN | 102161752 | 8/2011 |
| CN | 102702487 | 10/2012 |

OTHER PUBLICATIONS

Yoo, D. K.,"Synthesis of lactide from oligomeric PLA: effects of temperature, pressure, and catalyst." Macromolecular research 14.5 (2006): 510-516.*
International Search Report of PCT/CN2013/081710 dated Jan. 30, 2014, 6 pages.

* cited by examiner

*Primary Examiner* — Samantha Shterengarts
*Assistant Examiner* — Matt Mauro
(74) *Attorney, Agent, or Firm* — Rankin, Hill & Clark LLP

(57) ABSTRACT

A technological method for synthesizing optically pure L-/D-lactide by using a biogenic guanidine catalysis method. The method of the present invention comprises: by using biogenic guanidine creatinine (CR) as a catalyst and L-/D-lactic acid (90% of mass content) as a raw material, synthesizing optically pure L-/D-lactide by using a reactive reduced pressure distillation catalysis method. The method of the present invention has advantages that the used catalyst is biogenic guanidine creatinine and free of toxicity, metal, and cytotoxicity; the synthesized lactide is high in optical purity (the specific rotation of the L-lactide $[\alpha]25D=-276\sim-280$, and the specific rotation of the D-lactide $[\alpha]25D=280$), and does not contain any metal; the amount of the catalyst used in reaction is low, the technological process is simplified (a process for rectifying and purifying a crude lactide product by using a conventional method is avoided); and the technological method is simple and convenient to operate and easy in industrial implementation.

4 Claims, No Drawings

TECHNOLOGICAL METHOD FOR SYNTHESIS OF OPTICALLY PURE L-/D-LACTIDE CATALYZED BY BIOGENIC GUANIDINE

FIELD OF THE INVENTION

The present invention belongs to the field of optically pure monomer for synthesizing eco-friendly/biomedical biodegradable polylactic acid material, specifically the technological method for synthesizing optically pure L-/D-lactide by using biogenic guanidine creatinine (CR) as catalyst.

BACKGROUND OF THE INVENTION

Polylactic acid or poly lactide (PLA) is a kind of eco-friendly and biodegradable material, which can be used for preparing various kinds of medical materials, such as implantable hard tissue repair material, surgical suture, targeted and controlled release drug carrier, etc. In addition, polylactic acid can also be applied to the preparation of various biodegradable plastic products, such as films, fibers, packaging materials, etc. The production of commercially available polylactic acid is performed via catalyzed ring-opening polymerization using lactide as the monomer. Thus, the synthesis of lactide has an important significance for the production of polylactic acid. Optically pure lactide includes L-lactide and D-lactide. At present, the synthesis of commercially available L-/D-lactide is performed by the metal salt catalyst (e.g. stannous octoate, stannous chloride, etc., referring to U.S. Pat. No. 5,053,522). This method has the advantages: the metallic tin catalysts easily contaminate the products, not easy to regenerate, and possibly cause pollution to the environment, etc.

SUMMARY OF THE INVENTION

The object of the present invention is to solve the existing problems in the synthesis of commercially available L-/D-lactide such as easy contamination of product by the metallic tin catalyst, not easily regenerated, possible pollution to the environment, etc., and to provide a technological method for synthesizing optically pure L-/D-lactide by using biogenic guanidine catalysis method.

The technological method provided in the present invention is to synthesize the optically pure L-/D-lactide through the reactive reduced pressure distillation catalysis method using biogenic guanidine creatinine (arginine metabolites in the human body, the English abbreviation for CR) as a catalyst and L-/D-lactic acid (90% of mass content) as a raw material. The technological method for synthesizing L-/D-lactide comprises the following steps:

(1) Under the condition of heating temperature of 130° C.-170° C., L-/D-lactate was firstly reacted under normal pressure conditions for 1-4 h, then reacted 2-8 h under reduced pressure 30-60 torr, to produce lactic acid oligomers with the weight-average molecular weight of 600-1500 Da by dehydration and polycondensation.

(2) The lactic acid oligomers synthesized in step (1) was added to catalyst creatinine CR to react 1-4 h with the controlled temperature at 150-260° C. and degree of vacuum at 2-15 torr, and then the distilled white crude L-/D-lactide was collected.

(3) The crude L-/D-lactide collected in step (2) was washed using alkali with the mass concentration of 1-10% (sodium hydroxide, potassium hydroxide, sodium carbonate, potassium carbonate, sodium bicarbonate, or potassium bicarbonate), then washed to neutral using the deionized water, vacuum dried at 20° C.-40° C. for 24-36 h to get the lactide with high optical purity (specific rotation of L-lactide $[\alpha]25D=-276\sim-280$, specific rotation of D-lactide $[\alpha]25D=280$).

The mass ratio of organic guanidine catalyst creatinine CR to lactic acid oligomer in step (2) is within the range of 1:100-1:10000. In step (3), the impurities in the crude L-/D-lactide are removed by washing with the alkaline solution, to avoid the commonly-used crude distillation method for purification of crude lactide.

The advantages and beneficial effects of the present invention are as follows:

1. The used biogenic guanidine catalyst CR is free of toxicity, metal, and cytotoxicity;
2. the synthesized lactide is high in optical purity (the specific rotation of the L-lactide $[\alpha]25D=-276\sim-280$, and the specific rotation of the D-lactide $[\alpha]25D=280$), and does not contain any metal;
3. Short reaction time, less consumption of catalyst, simple technological process, easy to operate and easy for industrial practice.

DETAILED DESCRIPTION OF THE EMBODIMENTS

Example 1

① A reactor was charged with 100 g of L-lactic acid (90% by mass content). Under an argon atmosphere at normal pressure, the reaction system was then heated to 130 and subjected to dehydration for 4 h. The pressure in the reactor was then reduced to 60 Torr, reacting at 130° C. for 8 h, to get the lactic acid oligomer (OLLA), with a weight average molecular weight of 1500 Da.

The biogenic guanidine creatinine (CR) was added, to control the mass ratio of catalyst CR to L-lactic acid at 1:100, and the reaction temperature at 180, vacuum degree of 2 torr, to react 1 h; then the distilled white crude L-lactide was collected.

The collected crude L-lactide was washed with 1% alkali (sodium hydroxide) solution, cleaned with the deionized water to neutral, vacuum dried 24 h at 20° C., to get white needle L-lactide, with the yield of 35.5% and specific rotation $[\alpha]25D=-276$.

Example 2

① A reactor was charged with 100 g of L-lactic acid (90% by mass content). Under an argon atmosphere at normal pressure, the reaction system was then heated to 170 and subjected to dehydration for 1 h. The pressure in the reactor was then reduced to 30 torr, reacting at 170° C. for 2 h, to get the lactic acid oligomer (OLLA), with a weight average molecular weight of 600 Da.

The biogenic guanidine creatinine (CR) was added, to control the mass ratio of catalyst CR to L-lactic acid at 1:10000, and the reaction temperature at 260, vacuum degree of 15 torr, to react 4 h; then the distilled white crude L-lactide was collected.

The collected crude L-lactide was washed with 10% alkali (sodium carbonate) solution, cleaned with the deionized water to neutral, vacuum dried 36 h at 40° C., to get white needle L-lactide, with the yield of 40.3% and specific rotation $[\alpha]25D=-280$.

Example 3

① A reactor was charged with 100 g of L-lactic acid (90% by mass content). Under an argon atmosphere at normal pressure, the reaction system was then heated to 150 and subjected to dehydration for 2 h. The pressure in the reactor was then reduced to 40 Torr, reacting at 150° C. for 4 h, to get the lactic acid oligomer (OLLA), with a weight average molecular weight of 1100 Da.

The biogenic guanidine creatinine (CR) was added, to control the mass ratio of catalyst CR to L-lactic acid at 1:1000, and the reaction temperature at 200, vacuum degree of 10 torr, to react 3 h; then the distilled white crude L-lactide was collected.

The collected crude L-lactide was washed with 8% alkali (sodium bicarbonate) solution, cleaned with the deionized water to neutral, vacuum dried 30 h at 35° C., to get white needle L-lactide, with the yield of 45.8% and specific rotation [α] 25D=−277.

Example 4

① A reactor was charged with 100 g of L-lactic acid (90% by mass content). Under an argon atmosphere at normal pressure, the reaction system was then heated to 160 and subjected to dehydration for 2 h. The pressure in the reactor was then reduced to 50 Torr, reacting at 160° C. for 4 h, to get the lactic acid oligomer (OLLA), with a weight average molecular weight of 1300 Da.

The biogenic guanidine creatinine (CR) was added, to control the mass ratio of catalyst CR to L-lactic acid at 1:2000, and the reaction temperature at 220, vacuum degree of 8 torr, to react 2 h; then the distilled white crude L-lactide was collected.

The collected crude L-lactide was washed with 5% alkali (potassium bicarbonate) solution, cleaned with the deionized water to neutral, vacuum dried 26 h at 30° C., to get white needle L-lactide, with the yield of 40.8% and specific rotation [α] 25D=−280.

Example 5

① A reactor was charged with 100 g of L-lactic acid (90% by mass content). Under an argon atmosphere at normal pressure, the reaction system was then heated to 150 and subjected to dehydration for 1 h. The pressure in the reactor was then reduced to 30 Torr, reacting at 130° C. for 3 h, to get the lactic acid oligomer (OLLA), with a weight average molecular weight of 900 Da.

The biogenic guanidine creatinine (CR) was added, to control the mass ratio of catalyst CR to L-lactic acid at 1:5000, and the reaction temperature at 240, vacuum degree of 5 torr, to react 3 h; then the distilled white crude L-lactide was collected.

The collected crude L-lactide was washed with 2% alkali (potassium hydroxide) solution, cleaned with the deionized water to neutral, vacuum dried 35 h at 30° C., to get white needle L-lactide, with the yield of 38.8% and specific rotation [α] 25D=−277.

Example 6

① A reactor was charged with 100 g of L-lactic acid (90% by mass content). Under an argon atmosphere at normal pressure, the reaction system was then heated to 140 and subjected to dehydration for 2 h. The pressure in the reactor was then reduced to 30 Torr, reacting at 140° C. for 3 h, to get the lactic acid oligomer (OLLA), with a weight average molecular weight of 1200 Da.

The biogenic guanidine creatinine (CR) was added, to control the mass ratio of catalyst CR to L-lactic acid at 1:2000, and the reaction temperature at 250, vacuum degree of 3 torr, to react 4 h; then the distilled white crude L-lactide was collected.

The collected crude L-lactide was washed with 1% alkali (potassium carbonate) solution, cleaned with the deionized water to neutral, vacuum dried 24 h at 40° C., to get white needle L-lactide, with the yield of 42.4% and specific rotation [α] 25D=−280.

Example 7

① A reactor was charged with 100 g of D-lactic acid (90% by mass content). Under an argon atmosphere at normal pressure, the reaction system was then heated to 130 and subjected to dehydration for 3 h. The pressure in the reactor was then reduced to 60 Torr, reacting at 130° C. for 8 h, to get the lactic acid oligomer (ODLA), with a weight average molecular weight of 1500 Da.

The biogenic guanidine creatinine (CR) was added, to control the mass ratio of catalyst CR to D-lactic acid at 1:100, and the reaction temperature at 150, vacuum degree of 2 torr, to react 2 h; then the distilled white crude D-lactide was collected.

The collected crude D-lactide was washed with 1% alkali (potassium hydroxide) solution, cleaned with the deionized water to neutral, vacuum dried 24 h at 20° C., to get white needle D-lactide, with the yield of 41.7% and specific rotation [α] 25D=280.

Example 8

① A reactor was charged with 100 g of D-lactic acid (90% by mass content). Under an argon atmosphere at normal pressure, the reaction system was then heated to 170 and subjected to dehydration for 1 h. The pressure in the reactor was then reduced to 30 Torr, reacting at 170° C. for 4 h, to get the lactic acid oligomer (ODLA), with a weight average molecular weight of 800 Da.

The biogenic guanidine creatinine (CR) was added, to control the mass ratio of catalyst CR to D-lactic acid at 1:10000, and the reaction temperature at 260, vacuum degree of 15 torr, to react 4 h; then the distilled white crude L-lactide was collected.

The collected crude D-lactide was washed with 5% alkali (potassium carbonate) solution, cleaned with the deionized water to neutral, vacuum dried 36 h at 40° C., to get white needle D-lactide, with the yield of 40.3% and specific rotation [α] 25D=280.

Example 9

① A reactor was charged with 100 g of D-lactic acid (90% by mass content). Under an argon atmosphere at normal pressure, the reaction system was then heated to 150 and subjected to dehydration for 2 h. The pressure in the reactor was then reduced to 40 Torr, reacting at 150° C. for 4 h, to get the lactic acid oligomer (ODLA), with a weight average molecular weight of 1100 Da.

The biogenic guanidine creatinine (CR) was added, to control the mass ratio of catalyst CR to D-lactic acid at 1:1000, and the reaction temperature at 200, vacuum degree of 10 torr, to react 3 h; then the distilled white crude D-lactide was collected.

The collected crude D-lactide was washed with 6% alkali (potassium bicarbonate) solution, cleaned with the deionized water to neutral, vacuum dried 30 h at 35° C., to get white needle D-lactide, with the yield of 45.6% and specific rotation [α] 25D=280.

Example 10

① A reactor was charged with 100 g of D-lactic acid (90% by mass content). Under an argon atmosphere at normal pressure, the reaction system was then heated to 160 and subjected to dehydration for 2 h. The pressure in the reactor was then reduced to 50 Torr, reacting at 160° C. for 4 h, to get the lactic acid oligomer (ODLA), with a weight average molecular weight of 1300 Da.

The biogenic guanidine creatinine (CR) was added, to control the mass ratio of catalyst CR to D-lactic acid at 1:2000, and the reaction temperature at 200, vacuum degree of 8 torr, to react 2 h; then the distilled white crude D-lactide was collected.

The collected crude D-lactide was washed with 1% alkali (sodium hydroxide) solution, cleaned with the deionized water to neutral, vacuum dried 26 h at 30° C., to get white needle D-lactide, with the yield of 46.8% and specific rotation [α] 25D=280.

Example 11

① A reactor was charged with 100 g of D-lactic acid (90% by mass content). Under an argon atmosphere at normal pressure, the reaction system was then heated to 150 and subjected to dehydration for 1 h. The pressure in the reactor was then reduced to 30 Torr, reacting at 150° C. for 3 h, to get the lactic acid oligomer (ODLA), with a weight average molecular weight of 900 Da.

The biogenic guanidine creatinine (CR) was added, to control the mass ratio of catalyst CR to D-lactic acid at 1:5000, and the reaction temperature at 200, vacuum degree of 8 torr, to react 2 h; then the distilled white crude D-lactide was collected.

The collected crude D-lactide was washed with 1% alkali (sodium hydroxide) solution, cleaned with the deionized water to neutral, vacuum dried 35 h at 30° C., to get white needle D-lactide, with the yield of 44.5% and specific rotation [α] 25D=280.

Example 12

① A reactor was charged with 100 g of D-lactic acid (90% by mass content). Under an argon atmosphere at normal pressure, the reaction system was then heated to 140 and subjected to dehydration for 2 h. The pressure in the reactor was then reduced to 30 Torr, reacting at 140° C. for 3 h, to get the lactic acid oligomer (ODLA), with a weight average molecular weight of 1200 Da.

The biogenic guanidine creatinine (CR) was added, to control the mass ratio of catalyst CR to D-lactic acid at 1:2000, and the reaction temperature at 250, vacuum degree of 3 torr, to react 4 h; then the distilled white crude D-lactide was collected.

The collected crude D-lactide was washed with 6% alkali (sodium bicarbonate) solution, cleaned with the deionized water to neutral, vacuum dried 24 h at 40, to get white needle D-lactide, with the yield of 43.8% and specific rotation [α] 25D=280.

What is claimed is:

1. A method for synthesizing L-lactide or D-lactide comprising the following steps:
    (1) carrying out dehydration and polycondensation of L-lactate or D-lactate by:
        (1a) heating L-lactate or D-lactate at a temperature of 130° C.-170° C., at ambient pressure for 1-4 h, and
        (1b) heating the L-lactate or the D-lactate at a temperature of 130° C.-170° C. for 2-8 h at a pressure of 30-60 torr,
    to produce lactic acid oligomers with a weight-average molecular weight of 600-1500 Da;
    (2) carrying out catalytic distillation of the lactic acid oligomers from step (1) to form crude L-lactide or D-lactide by:
        (2a) mixing the lactic acid oligomers from step (1) with creatinine catalyst; and
        (2b) reacting the mixture for 1-4 h at a temperature of 150-260° C. and a pressure of 2-15 torr,
    to produce distilled white crude L-lactide or D-lactide;
    (3) washing the crude L-lactide or D-lactide from step (2) with an alkaline solution having a mass concentration of 1-10% alkali, then washing to neutral using deionized water, and
    (4) vacuum drying the washed L-lactide or D-lactide at 20° C.-40° C. for 24-36 h to thereby obtain L-lactide or D-lactide.

2. The method according to claim 1, wherein the specific rotation [α]25D of L-lactide is −276 to −280, and the specific rotation [α]25D of D-lactide=280.

3. The method according to claim 1, wherein the mass ratio of creatinine catalyst to lactic acid oligomers in step (2) is within the range of 1:100-1:10000.

4. The method according to claim 1, wherein the alkaline solution with mass concentration of 1-10% in step (3) is a solution of sodium hydroxide, potassium hydroxide, sodium carbonate, potassium carbonate, sodium or potassium bicarbonate; and
    wherein washing with the alkaline solution removes impurities in the crude L-lactide or D-lactide.

* * * * *